(12) United States Patent
Ford et al.

(10) Patent No.: US 9,796,737 B2
(45) Date of Patent: Oct. 24, 2017

(54) METHOD FOR PRODUCING 1-INDANOLES AND 1-INDANAMINES

(71) Applicant: Bayer CropScience Aktiengesellschaft, Monheim am Rhein (DE)

(72) Inventors: Mark James Ford, Wiesbaden-Breckenheim (DE); Jean-Pierre Vors, Saint Foy les Lyon (FR); Olivier Baudoin, Mulhouse (FR); Simon Janody, Le Noirmont (CH)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 15/114,385

(22) PCT Filed: Jan. 23, 2015

(86) PCT No.: PCT/EP2015/051344
§ 371 (c)(1),
(2) Date: Jul. 26, 2016

(87) PCT Pub. No.: WO2015/113903
PCT Pub. Date: Aug. 6, 2015

(65) Prior Publication Data
US 2016/0340370 A1 Nov. 24, 2016

(30) Foreign Application Priority Data
Jan. 28, 2014 (EP) .................................. 14152790

(51) Int. Cl.
C07F 7/04 (2006.01)
C07F 7/08 (2006.01)
C07C 209/58 (2006.01)
C07D 209/48 (2006.01)
C07F 7/18 (2006.01)
C07C 67/297 (2006.01)

(52) U.S. Cl.
CPC .......... *C07F 7/0818* (2013.01); *C07C 67/297* (2013.01); *C07C 209/58* (2013.01); *C07D 209/48* (2013.01); *C07F 7/1844* (2013.01); *C07F 7/1872* (2013.01); *C07B 2200/07* (2013.01); *C07C 2602/08* (2017.05)

(58) Field of Classification Search
CPC .. C07D 307/93; C07D 209/48; C07C 209/58; C07F 7/18
USPC ........................................................ 556/445
See application file for complete search history.

(56) References Cited

FOREIGN PATENT DOCUMENTS

| NO | 2004069814 A1 | 8/2004 |
|---|---|---|
| NO | 2007112834 A2 | 3/2007 |

OTHER PUBLICATIONS

Pierre et al., Org. Lett., 13(7), 2011, pp. 1816-1819.*
Cathleen Pierre et al.; "Synthesis of Polycyclic Molecules by Double C(sp2)-H/C(sp3)-H Arylations with a Single Palladium Catalyst"; Institut de Chimie et Biochimie Moleculaires et Supramoleculaires, CPE Lyon, vol. 3; No. 7; pp. 1816-1819; Feb. 3, 2011.
Nicolas Martin et al.; "Diastereo- and Enantioselective Intramolecular C(sp3)-H Arylationa for the Synthesis of used Cyclopentanes"; Chemistry—a European Journal; DOI: 10.1002/chem.201200018; pp. 4480-4484; 2012.
J.A. Pincock et al.; "The Photochemistry of Conformationally Rigid Benzylic Esters: 2,2-Dimethyl-1-indanyl Acetates and Pivalates"; Department of Chemistry; J. Org. Chem. 1995; vol. 60, pp. 4067-4076.
Hui Fang et al.; "Rapid Catalyst Screening by a Continuous-Flow Microreactor Interfaces with Ultra-High-Pressure Liquid Chromatography"; Department of Chemistry, University of Pittsburgh, PA 15260; J. Org. Chem. May 19, 2010; pp. 5619-5626.
International Search Report dated Mar. 25, 2015.

* cited by examiner

Primary Examiner — Sudhakar Katakam
Assistant Examiner — Kofi Adzamli
(74) Attorney, Agent, or Firm — McBee Moore Woodward & Vanik IP, LLC; Susan McBee; David Woodward

(57) ABSTRACT

A description is given of a process for preparing 1-indanols and 1-indanamines by palladium-catalyzed arylation and of the use thereof as intermediates for the synthesis of fine chemicals and of active agrochemical ingredients.

11 Claims, No Drawings

METHOD FOR PRODUCING 1-INDANOLES AND 1-INDANAMINES

CROSS-REFERENCE TO RELATED APPLICATIONS

This application is a §371 National Stage Application of PCT/EP2015/051344, filed Jan. 23, 2015, which claims priority to EP 14152790.3, filed Jan. 28, 2014.

DESCRIPTION

The invention relates to a process for preparing 1-indanols and 1-indanamines by palladium-catalyzed arylation and to the use thereof as intermediates for the synthesis of fine chemicals and of active agrochemical ingredients.

1-Indanols and 1-indanamines of the formula (I), in which Y is a substituted hydroxyl or amino group, constitute an important structural element in a multitude of agronomically active substances, as disclosed, for example, in WO 2004/069814 A1 and WO 2007/112834 A1.

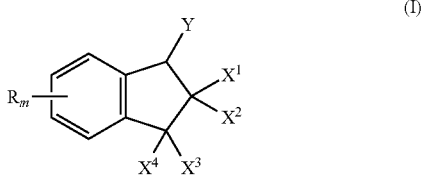

J. A. Pincock et al.: "The Photochemistry of Conformationally Rigid Benzylic Esters: 2,2-Dimethyl-1-indanyl Acetates and Pivalates", *The Journal of Organic Chemistry* 1995, 13, 4067, describe the preparation of 1-indanols by reduction of the corresponding 1-indanones.

Hui Fang et al.: "Rapid Catalyst Screening by a Continuous-Flow Microreactor Interfaced with Ultra-High-Pressure Liquid Chromatography", *The Journal of Organic Chemistry* 2010, 16, 5619, describe the synthesis of an indanamine starting from the corresponding 3-(3,4-dimethoxyphenyl)-2,2-dimethylpropanenitrile or from an acylaminal precursor.

From C. Pierre, O. Baudoin, *Org. Lett.* 2011 13, 1816 and N. Martin, C. Pierre, M. Davi, R. Jazzar, O. Baudoin, *O. Chem.-Eur. J.* 2012, 18, 4480, palladium(0)-catalyzed arylations of 2-haloketones (IIa) or 2-halo compounds (IIb) are known. The starting compounds (IIa) and (IIb) are in both cases compounds in which there is a carbon atom in the 2-position relative to the halogen atom on the phenyl ring that does not carry a hydrogen atom (C=O in formula IIa and CRY, with R and Y each being other than hydrogen, in formula IIb):

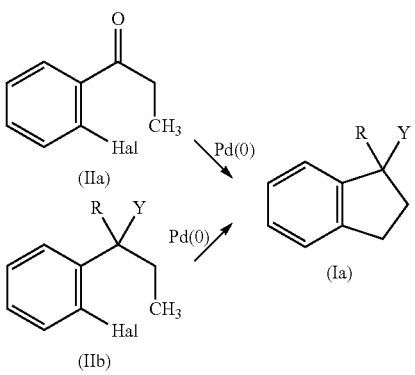

However, the processes specified in these documents for preparing 1-indanols and 1-indanamines are restricted to performance on the laboratory scale, since they have a number of disadvantages and are thus unusable for industrial production. A further very significant disadvantage of the known prior art processes via palladium-catalyzed arylation of 2-halo compounds is the fact that they have so far been described solely for starting compounds (IIa) and (IIb) in which there is a carbon atom in the 2-position relative to the halogen atom on the phenyl ring that does not carry a hydrogen atom, and so lead to formation of 1-indanols and 1-indanamines (Ia) in which R is not hydrogen.

For preparing the abovementioned agronomically active substances, however, it is the 1-indanols and 1-indanamines of the formula (I) that are of interest as intermediates, i.e., those in which the carbon atom substituted by the radical Y still carries a hydrogen atom.

SUMMARY

It is an object of the present invention to provide a process for preparing 1-indanols and 1-indanamines which overcomes the disadvantages of the processes known from the prior art.

It has now been found that 1-indanols and 1-indanamines can be prepared in high yields by palladium-catalyzed arylation of 1-(2-halophenyl)alkan-1-ols or 1-(2-halophenyl)alkan-1-amines.

The present invention accordingly provides a process for preparing 1-indanols and 1-indanamines of the general formula (I) which comprises reacting 1-(2-halophenyl)alkan-1-ols or 1-(2-halophenyl)alkan-1-amines (II) at elevated temperature under palladium catalysis in the presence of phosphine ligands, a base, and a solvent,

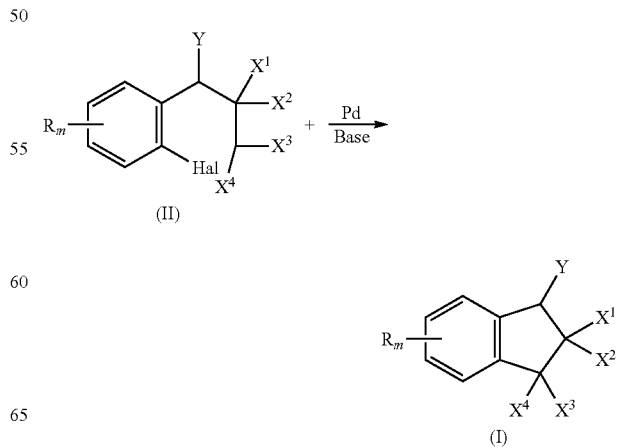

and in which the radicals, symbols, and indices are defined as follows:

Y is $NR^1R^2$ or $OR^3$,
$R^1$ is hydrogen or $COR^4$,
$R^2$ is $COR^4$,
or $R^1$ and $R^2$ together form the group $COCH_2CH_2CO$ or CO-phenylene-CO,
$R^3$ is $Si(R^5)_3$ or pivaloyl (2,2-dimethylpropanoyl),
$R^4$ is $(C_1-C_6)$-alkyl or phenyl,
$R^5$ is $(C_1-C_6)$-alkyl or phenyl,
Hal is chlorine, bromine or iodine,
R is fluorine, $(C_1-C_3)$-alkyl or $(C_1-C_3)$-alkoxy,
$X^1$ is hydrogen or $(C_1-C_6)$-alkyl,
$X^2$ is hydrogen or $(C_1-C_6)$-alkyl,
$X^3$ is hydrogen or $(C_1-C_6)$-alkyl,
$X^4$ is hydrogen or $(C_1-C_6)$-alkyl,
or
$X^1$ and $X^2$, or
$X^3$ and $X^4$, or
$X^1$ and $X^3$ together with the carbon atom to which they are bonded form in each case a 3- to 7-membered saturated ring,
or
Y and $X^1$ together with the carbon atoms to which they are bonded form a 5- to 7-membered saturated ring,
m is 0, 1, 2 or 3.

DETAILED DESCRIPTION OF A PREFERRED EMBODIMENT

Suitable palladium catalysts are, for example, Pd(OAc)2, Pd2dba3 (tris(dibenzylideneacetone)dipalladium(0)), PdCl2, and PdBr2, with Pd(OAc)2 being preferred. The palladium catalyst is used customarily in an amount of 0.1 to 10 mol %, preferably 1 to 10 mol %, more preferably 1 to 5 mol %, based on the compound (II).

Suitable phosphine ligands are, for example, trialkylphosphines, tricycloalkylphosphines such as tricyclohexylphosphine, triarylphosphines such as triphenylphosphine, tri-ortho-tolylphosphine, tri(4-dimethylaminophenyl) phosphines, and alkyldiarylphosphines such as butyldiphenylphosphine, with triphenylphosphine being particularly preferred. The phosphines may also be used in the form of salts, with HBF4, for example, The phosphine ligands are used customarily in an amount of 0.1 to 10 mol %, preferably 1 to 10 mol %, more preferably 1 to 5 mol %, based on the compound (II).

Palladium catalysts and phosphine ligands can be used as separate compounds or usefully in the form of a preformed complex—for example, as tetrakis(triphenylphosphinyl)palladium, which is particularly preferred.

Suitable bases are, for example, carbonates, hydrogencarbonates, phosphates, alkoxides, and carboxylates of alkali metals, such as $Li_2CO_3$, $Na_2CO_3$, $K_2CO_3$, $NaHCO_3$, $KHCO_3$, $K_3PO_4$, $K_2HPO_4$, NaOMe, NaOEt, NaOiPr, NaOtBu, KOMe, KOEt, KOiPr, KOtBu, NaOAc, KOAc, NaOPiv (sodium pivalate), KOPiv. NaOCOPh, and KOCOPh or mixtures of such bases. Mixtures of carbonates and carboxylates are preferred. The mixture of $K_2CO_3$ and KOPiv is particularly preferred. The base is used customarily in a 1- to 5-molar proportion, based on the compound (II).

Suitable solvents are, for example, aromatics such as toluene, xylene, chlorobenzene, and anisole; ethers such as dibutyl ether, diphenyl ether, and polyglycol ethers; esters such as butyl acetate and isopropyl acetate; amides such as dimethylacetamide, dimethylformamide, and dibutylformamide, or mixtures thereof. Particularly preferred are aromatic solvents such as xylene.

The preparation process of the invention is carried out customarily at elevated temperature of more than 100° C. up to the boiling point of the solvent in question. A range from 120 to 150° C. is preferred, Should the boiling point of the solvent in question be below this, it is useful to work under superatmospheric pressure.

The process is carried out preferably for compounds of the formulae specified above in which the radicals, symbols, and indices are defined as follows:

Y is $NR^1R^2$ or $OR^3$,
$R^1$ is hydrogen or $COR^4$,
$R^2$ is $COR^4$,
$R^3$ is $Si(R^5)_3$ or 2,2-dimethylpropanoyl,
$R^4$ is tert-butyl,
$R^5$ is isopropyl,
Hal is bromine or iodine,
R is fluorine, methyl or methoxy,
$X^1$ is hydrogen or methyl,
$X^2$ is hydrogen or methyl,
$X^3$ is hydrogen or methyl,
$X^4$ is hydrogen or methyl,
or
$X^1$ and $X^2$, or
$X^3$ and $X^4$, or
$X^1$ and $X^3$ together with the carbon atom to which they are bonded form in each case a 3- to 7-membered saturated ring,
or
Y and $X^1$ together with the carbon atoms to which they are bonded form a 5- to 7-membered saturated ring,
m is 0, 1, 2 or 3.

In the formula (I) and all the formulae which follow, alkyl radicals having more than two carbon atoms may be straight-chain or branched. Alkyl radicals are, for example, methyl, ethyl, n- or isopropyl, n-, iso-, tert- or 2-butyl, pentyls, and hexyls, such as n-hexyl, isohexyl, and 1,3-dimethylbutyl.

The examples which follow illustrate the invention.

The abbreviations used here are:

| Ac | acetate | Cy | cyclohexyl | Cyp | cyclopentyl |
|---|---|---|---|---|---|
| Me | methyl | Ph | phenyl | Piv | pivalate |
| TiPs | triisopropylsilyl | | | | |

General instructions:

Under inert gas, the palladium catalyst (0.015 mmol, 5 mol %), optionally the phosphine ligand (0.03 mmol, 10 mol %), and the base, e.g., potassium pivalate (0.030 mmol, 10 mol %) and $K_2CO_3$ (0.3 mmol, 1.0 eq) are introduced and the solvent (3 ml of xylene) and a compound of the formula (II) (0.3 mmol, 1.0 eq) are added. The mixture is then stirred at room temperature for 10 minutes and subsequently heated to 140° C. and stirred at this temperature for 16 hours. After the reaction mixture has cooled to room temperature it is filtered, the solvent is stripped off, and the residue is purified by chromatography.

EXAMPLE 1

Preparation of 2,2-dimethyl-2,3-dihydro-1H-inden-1-yl)oxy)triisopropylsilane from [1-(2-bromophenyl)-2,2-dimethylpropoxy](triisopropyl)silane

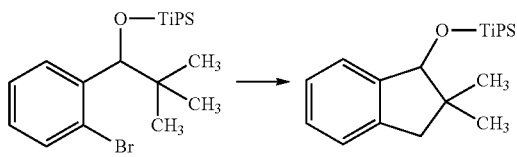

The reaction took place in line with the general instructions, with 5 mol % of Pd(PPh$_3$)$_4$, and gave a yield of 89%.
$^1$H NMR (300 MHz, CDCl$_3$, 293 K) δ 1.01 (s, 3H), 1.06-1.25 (m, 24H), 2.60 (d, J=15.2 Hz, 1H), 2.75 (d, J=15.2 Hz, 1H), 4.93 (s, 1H), 7.11-7.22 (m, 3H), 7.29-7.38 (m, 1H).

EXAMPLE 2

Preparation of ((2',3'-dihydrospiro[cyclopropane-1,1'-inden]-3'-yl)oxy)triisopropylsilane from [1-(2-bromophenyl)-cyclopropylethoxy](triisopropyl)silane

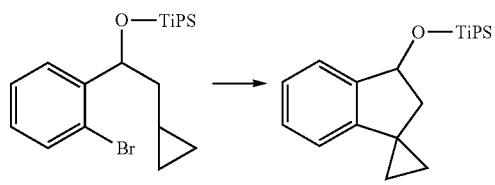

The reaction took place in line with the general instructions, with 5 mol % of Pd(PPh$_3$)$_4$, and gave a yield of 69%.
$^1$H NMR (300 MHz, CDCl$_3$, 293 K) δ 0.70-0.82 (m, 1H), 0.85-0.96 (m, 1H), 1.00-1.27 (m, 23H), 2.31 (d, J=7.2 Hz, 2H), 5.60 (t, J=7.2 Hz, 1H), 6.67-6.76 (m, 1H), 7.17-7.27 (m, 2H), 7.39-7.46 (m, 1H).

EXAMPLE 3

Preparation of ((5,6-dimethoxy-2,2-dimethyl-2,3-dihydro-1H-inden-1-yl)oxy)triisopropylsilane from [1-(2-bromo-4,5-dimethoxyphenyl)-2,2-dimethylpropoxy](tri-tert-butypsilane

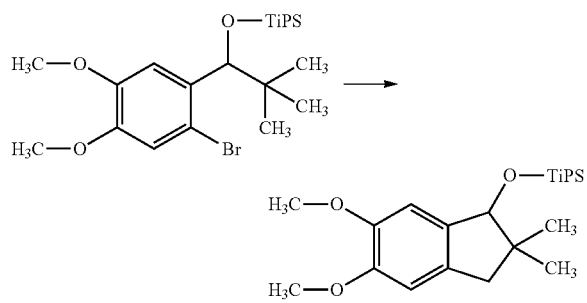

The reaction took place in line with the general instructions, with 5 mol % of Pd(PPh$_3$)$_4$, and gave a yield of 84%.
$^1$H NMR (300 MHz, CDCl$_3$, 293 K) δ 1.02 (s, 3H), 1.06-1.25 (m, 24H), 2.53 (d, J=15.0 Hz, 1H), 2.69 (d, J=15.0 Hz, 1H), 3.85 (s, 6H), 4.86 (s, 1H), 6.69 (s, 1H), 6.89 (s, 1H).

EXAMPLE 4

Preparation of ((6-methoxy-2,2-dimethyl-2,3-dihydro-1H-inden-1-yl)oxy)triisopropylsilane from [1-(2-bromo-5-methoxyphenyl)-2,2-dimethylpropoxy](tri-tert-butyl)silane

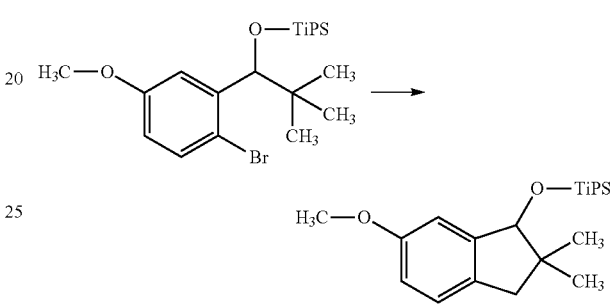

The reaction took place in line with the general instructions, with 5 mol % of Pd(PPh$_3$)$_4$, and gave a yield of 81%.
$^1$H NMR (300 MHz, CDCl$_3$, 293 K) δ 0.98 (s, 3H), 1.05-1.28 (m, 24H), 2.54 (d, J=14.8 Hz, 1H), 2.65 (d, J=14.8 Hz, 1H), 3.79 (s, 3H), 4.90 (s, 1H), 6.73 (dd, J=2.5, 8.1 Hz, 1H), 6.89 (d, J=2.5 Hz, 1H), 7.04 (d, J=8.1 Hz, 1H).

EXAMPLE 5

Preparation of ((6-fluoro-2,2-dimethyl-2,3-dihydro-1H-inden-1-yl)oxy)triisopropylsilane from [1-(2-bromo-5-fluorophenyl)-2,2-dimethylpropoxy](tri-tert-butyl)silane

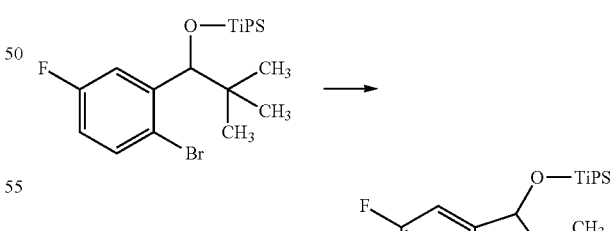

The reaction took place in line with the general instructions, with 5 mol % of Pd(PPh$_3$)$_4$, and gave a yield of 84%.
$^1$H NMR (300 MHz, CDCl$_3$, 293 K) δ1.00 (s, 3H), 1.06-1.26 (m, 24H), 2.55 (d, J=15.0 Hz, 1H), 2.68 (d, J=15.0 Hz, 1H), 4.90 (s, 1H), 6.87 (ddd, J=2.5, 81, 9.2 Hz, 1H), 7.00 (dd, J=2.5, 8.7 Hz, 1H), 7.07 (dd, J=5.2, 8.1 Hz, 1H).

EXAMPLE 6

Preparation of 2,2-dimethyl-2,3-dihydro-1H-inden-1-yl 2,2-dimethylpropanoate from 1-(2-bromophenyl)-2,2-dimethylpropyl 2,2-dimethylpropanoate

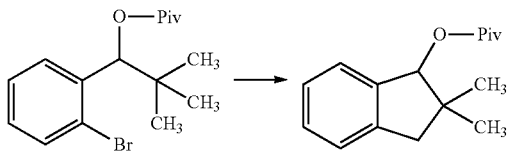

The reaction took place in line with the general instructions, with 5 mol % of Pd(PPh$_3$)$_4$, and gave a yield of 95%.

$^1$H NMR (300 MHz, CDCl$_3$, 293 K) δ 1.09 (s, 3H), 1.16 (s, 3H), 1.21 (s, 9H), 2.69 (d, J=15.3 Hz, 1H), 2.87 (d, J=15.3 Hz, 1H), 5.81 (s, 1H), 7.09-7.29 (m, 4H).

EXAMPLE 7

Preparation of 6-methoxy-2,2-dimethyl-2,3-dihydro-1H-inden-1-yl 2,2-dimethylpropanoate from 1-(2-bromo-5-methoxyphenyl)-2,2-dimethylpropyl 2,2-dimethylpropanoate

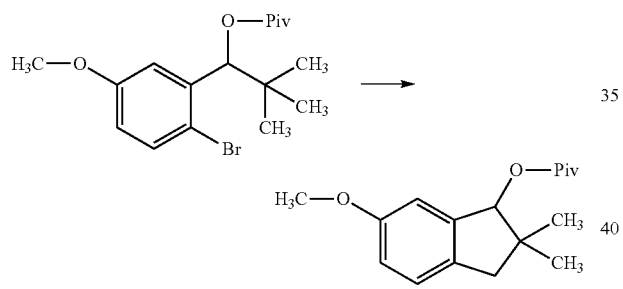

The reaction took place in line with the general instructions, with 5 mol % of Pd(PPh$_3$)$_4$, and gave a yield of 88%.

$^1$H NMR (300 MHz, CDCl$_3$, 293 K) δ 1.09 (s, 3H), 1.16 (s, 3H), 1.22 (s, 9H), 2.63 (d, J=15.3 Hz, 1H), 2.80 (d, J=15.3 Hz, 1H), 3.77 (s, 3H), 5.79 (s, 1H), 6.77-6.84 (m, 2H), 7.05-7.12 (m, 1H).

EXAMPLE 8

Preparation of 6-fluoro-2,2-dimethyl-2,3-dihydro-1H-inden-1-yl 2,2-dimethylpropanoate from 1-(2-bromo-5-fluorophenyl)-2,2-dimethylpropyl 2,2-dimethylpropanoate

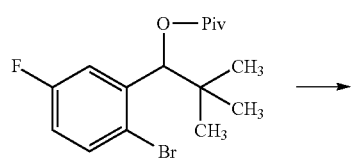

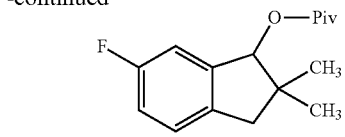

The reaction took place in line with the general instructions, with 5 mol % of Pd(PPh$_3$)$_4$, and gave a yield of 76%.

$^1$H NMR (300 MHz, CDCl$_3$, 293 K) δ 1.08 (s, 3H), 1.16 (s, 3H), 1.22 (s, 9H), 2.65 (d, J=15.4 Hz, 1H), 2.81 (d, J=15.4 Hz, 1H), 5.76 (s, 1H), 6.87-6.99 (m, 2H), 7.08-7.15 (m, 1H).

EXAMPLE 9

Preparation of (3aR*,8bS*)-3a-methyl-3,3a,4,8b-tetrahydro-2H-indeno[1,2-b]furan-2-one from 5-(2-bromophenyl)-4,4-dimethyldihydrofuran-2(3H)-one

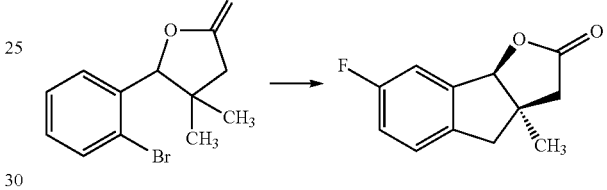

The reaction took place in line with the general instructions, with 5 mol % of Pd(PPh$_3$)$_4$, and gave a yield of 88%.

$^1$H NMR (300 MHz, CDCl$_3$, 293 K) δ 1.34 (s, 3H), 2.45 (d, J=17.8 Hz, 1H), 2.51 (d, J=17.8 Hz, 1H), 2.87 (d, J=16.4 Hz, 1H), 3.00 (d, J=16.4 Hz, 1H), 5.32 (s, 1H), 7.13-7.29 (m, 3H), 7.36 (d, J=7.2 Hz, 1H).

EXAMPLE 10

Preparation of 2-(2-methyl-2,3-dihydro-1H-inden-1-yl)isoindoline-1,3-dione from 2-[1-(2-bromophenyl)-2-methylpropyl]-1H-isoindole-1,3(2H)-dione

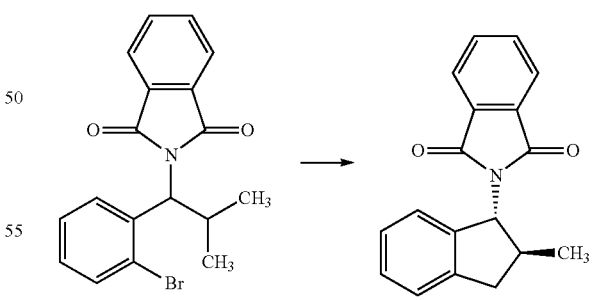

The reaction took place in line with the general instructions, with 5 mol % of Pd(PPh$_3$)$_4$, and gave a yield of 54% of the trans isomer.

$^1$H NMR (300 MHz, CDCl$_3$, 293 K) δ 1.27 (d, J=6.8 Hz, 3H), 2.65 (dd, J=8.6, 15.6 Hz, 1H), 3.00-3.18 (m, 1H), 3.37 (dd, J=8.2, 15.6 Hz, 1H), 5.43 (d, J=8.2 Hz, 1H), 7.01 (d, J=7.6 Hz, 1H), 7.11-7.19 (m, 1H), 7.20-7.30 (m, 2H), 7.70-7.79 (m, 2H), 7.82-7.91 (m, 2H).

EXAMPLE 11

Preparation of 2-(2,2-dimethyl-2,3-dihydro-1H-inden-1-yl)isoindoline-1,3-dione from 2-[1-(2-bromophenyl)-2,2-dimethylpropyl]-1H-isoindole-1,3(2H)-dione

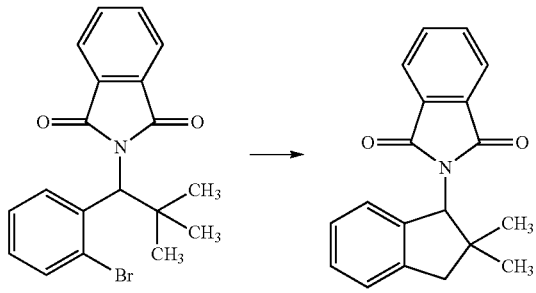 [SMILES: CC(C)(C)C(c1ccccc1Br)N1C(=O)c2ccccc2C1=O ; CC1(C)Cc2ccccc2C1N1C(=O)c2ccccc2C1=O]

The reaction took place in line with the general instructions, with 5 mol % of Pd(PPh₃)₄, and gave a yield of 86%.

¹H NMR (300 MHz, CDCl₃, 293 K) δ 0.64 (s, 3H), 0.83 (s, 3H), 2.34 (d, J=15.6 Hz, 1H), 2.87 (d, J=15.6 Hz, 1H), 4.9 (s, 1H), 6.66-6.77 (m, 2H), 6.80-6.89 (m, 2H), 7.16-7.33 (m, 3H), 7.42-7.49 (m, 1H).

EXAMPLE 12

Preparation of (1R,2S)-2,6-dimethylindan-1-amine from 2-[1-(2-bromo-5-methylphenyl)-2-methylpropyl]-1H-isoindole-1,3(2H)-dione via 2-[(1R,2S)-2,6-dimethyl-2,3-dihydro-1H-inden-1-yl]-1H-isoindole-1,3(2H)-dione

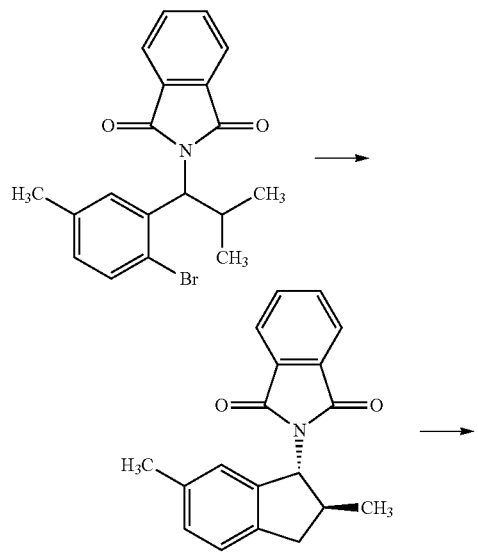

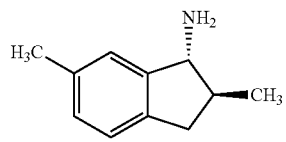

The reaction took place initially in line with the general instructions, with 5 mol % of Pd(PPh₃)₄, and gave a yield of 55% of the primary product.

¹H NMR (300 MHz, CDCl₃, 293 K) δ 1.24 (d, J=7.0 Hz, 3H), 2.25 (s, 3H), 2.58 (dd, J=8.0, 15.7 Hz, 1H), 2.97-3.15 (m, 1H), 3.32 (dd, J=8.2, 15.7 Hz, 1H), 5.37 (d, J=8.2 Hz, 1H), 6.80 (s, 1H), 7.03 (d, J=7.5 Hz, 1H), 7.14 (d, J=7.5 Hz, 1H), 7.70-7.78 (m, 2H), 7.80-7.90 (m, 2H).

Then a solution of 0.17 mmol of 2-(2,6-dimethyl-2,3-dihydro-1H-inden-1-yl)isoindoline-1,3-dione in 1 ml of methanol and 1 ml of THF was admixed at 0° C. with 1.7 mmol of hydrazine hydrate. The mixture was then stirred at room temperature for 12 hours. The mixture was filtered and concentrated, The residue was partitioned between DCM and water, and the organic phase was isolated and washed with saturated NaHCO₃. After drying over MgSO₄ and concentration, the product was obtained as a solid with a yield of 98%.

¹H NMR (300 MHz, CDCl₃, 293 K) δ 1.25 (d, J=6.7 Hz, 3H), 1.68 (s, 2H), 1.90-2.08 (m, 1H), 2.35 (s, 3H), 2.44 (dd, J=9.5, 15.3 Hz, 1H), 2.99 (dd, J=7.7, 15.3 Hz, 1H), 3.76 (d, J=8.3 Hz, 1H) 7.01 (d, J=7.5 Hz, 1H), 7.08 (d, J=7.5 Hz, 1H), 7.13 (s, 1H).

EXAMPLE 13

Preparation of triisopropyl((2-methyl-2,3-dihydro-1H-inden-1-yl)oxy)silane from [1-(2-bromophenyl)-2-methylpropoxy](triisopropyl)silane

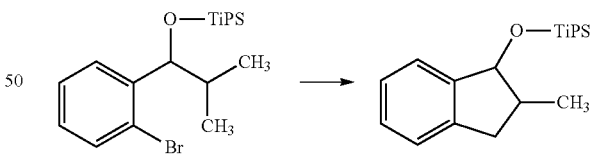

This reaction was executed with different palladium catalysts, phosphine ligands, and quantities of bases. The results of these experiments, achieved under various conditions, are set out in table form:

| No. | Pd cat. | Phosphine | K₂CO₃ | KOPiv | Yield of theory |
|---|---|---|---|---|---|
| 13a | 5 mol % Pd(PPh₃)₄ | | 100 mol % | 10 mol % | 55% cis, 8% trans |
| 13b | 5 mol % Pd(OAc)₂ | 10 mol % PCy₃ | 110 mol % | 10 mol % | 47% cis, 5% trans |
| 13c | 5 mol % Pd(OAc)₂ | 10 mol % PCyp₃ | 110 mol % | 10 mol % | 41% cis, 5% trans |
| 13d | 5 mol % Pd(OAc)₂ | 10 mol % PPh₃ | 100 mol % | 10 mol % | 57% cis, 6% trans |

| No. | Pd cat. | Phosphine | $K_2CO_3$ | KOPiv | Yield of theory |
|---|---|---|---|---|---|
| 13e | 5 mol % Pd(OAc)$_2$ | 10 mol % P(4-Me$_2$N—Ph)$_3$ | 100 mol % | 10 mol % | 48% cis, 9% trans | cis isomer: $^1$H NMR (300 MHz, CDCl$_3$, 293 K) δ 0.99 (d, J=6.9 Hz, 3H), 1.08-1.25 (m, 21H), 2.56-2.68 (m, 2H), 2.92 (dd, J=7.1, 15.7 Hz, 1H), 5.29 (d, J=5.8 Hz, 1H), 7.17-7.25 (m, 3H), 7.35-7.43 (m, 1H).

trans isomer: $^1$H NMR (300 MHz, CDCl$_3$, 293 K) δ 1.05-1.31 (m, 24H), 2.34-2.57 (m, 2H), 3.10-3.33 (m, 1H), 4.98 (d, J=5.0 Hz, 1H), 7.19-7.28 (m, 3H), 7.37-7.46 (m, 1H).

What is claimed is:

1. A process for preparing a 1-indanol and/or a 1-indanamine of formula (I) which comprises reacting a 1-(2-halophenyl)alkan-1-ol or 1-(2-halophenyl)alkan-1-amine (II) at elevated temperature under palladium catalysis in the presence of one or more phosphine ligands, a base, and a solvent,

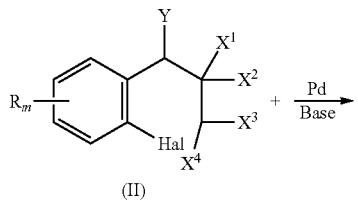

and in which the radicals, symbols, and indices are defined as follows:

Y is NR$^1$R$^2$ or OR$^3$,
R$^1$ is hydrogen or COR$^4$,
R$^2$ is COR$^4$,
or R$^1$ and R$^2$ together form the group COCH$_2$CH$_2$CO or CO-phenylene-CO,
R$^3$ is Si(R$^5$)$_3$ or 2,2-dimethylpropanoyl,
R$^4$ is (C$_1$-C$_6$)-alkyl or phenyl,
R$^5$ is (C$_1$-C$_6$)-alkyl or phenyl,
Hal is chlorine, bromine or iodine,
R is fluorine, (C$_1$-C$_3$)-alkyl or (C$_1$-C$_3$)-alkoxy,
X$^1$ is hydrogen or (C$_1$-C$_6$)-alkyl,
X$^2$ is hydrogen or (C$_1$-C$_6$)-alkyl,
X$^3$ is hydrogen or (C$_1$-C$_6$)-alkyl,
X$^4$ is hydrogen or (C$_1$-C$_6$)-alkyl,
or
X$^1$ and X$^2$, or
X$^3$ and X$^4$, or
X$^1$ and X$^3$ together with the carbon atom to which they are bonded form in each case a 3- to 7-membered saturated ring,
or
Y and X$^1$ together with the carbon atoms to which they are bonded form a 5- to 7-membered saturated ring,
m is 0, 1, 2 or 3.

2. The process as claimed in claim 1, in which the radicals, symbols, and indices have the following definitions:
Y is NR$^1$R$^2$ or OR$^3$,
R$^1$ is hydrogen or COR$^4$,
R$^2$ is COR$^4$,
R$^3$ is Si(R$^5$)$_3$ or 2,2-dimethylpropanoyl,
R$^4$ is tert-butyl,
R$^5$ isisopropyl,
Hal is bromine or iodine,
R is fluorine, methyl or methoxy,
X$^1$ is hydrogen or methyl,
X$^2$ is hydrogen or methyl,
X$^3$ is hydrogen or methyl,
X$^4$ is hydrogen or methyl,
or
X$^1$ and X$^2$, or
X$^3$ and X$^4$, or
X$^1$ and X$^3$ together with the carbon atom to which they are bonded form in each case a 3- to 7-membered saturated ring,
or
Y and X$^1$ together with the carbon atoms to which they are bonded form a 5- to 7-membered saturated ring,
m is 0, 1, 2 or 3.

3. The process as claimed in claim 1, in which said palladium catalyst used is a compound from the group consisting of Pd(OAc)$_2$, tris(dibenzylideneacetone)dipalladium(0), PdCl$_2$, and PdBr$_2$.

4. The process as claimed in claim 3, in which Pd(OAc)$_2$ is used.

5. The process as claimed in claim 1, in which triphenylphosphine is used as ligand.

6. The process as claimed in claim 1, in which tetrakis(triphenylphosphinyl)palladium is used as combined palladium catalyst and ligand.

7. The process as claimed in claim 1, in which the palladium catalyst and the ligand or the combination thereof are/is used in each case in an amount of 0.1 to 10 mol %, based on the compound (II).

8. The process as claimed in claim 7, in which the palladium catalyst and the ligand or the combination thereof are/is used in each case in an amount of 1 to 5 mol %, based on the compound (II).

9. The process as claimed in claim 1, where said base used is a mixture of an alkali metal carbonate and an alkali metal pivalate.

10. The process as claimed in claim 1, where the base is used in a 1- to 5-molar proportion, based on the compound (II).

11. The process as claimed in claim 1, where said solvent used is from the group of the aromatics.

* * * * *